(12) United States Patent
Lanter et al.

(10) Patent No.: US 6,228,986 B1
(45) Date of Patent: May 8, 2001

(54) SOLID-PHASE SYNTHESIS OF NOVEL 14-MEMBERED MACROYCLES FOR HIGH THROUGHPUT SCREENING

(75) Inventors: Carolina L. Lanter, Hillsborough; Joseph W. Guiles, Bedminster, both of NJ (US); Ralph A. Rivero, North Wales, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/287,902

(22) Filed: Apr. 7, 1999

Related U.S. Application Data

(60) Provisional application No. 60/081,501, filed on Apr. 13, 1998.

(51) Int. Cl.[7] .............................. A61K 38/12; C07K 5/00; C07K 16/00; C07K 17/00; G01N 33/543
(52) U.S. Cl. ..................... 530/317; 424/177; 435/7.1; 435/7.2; 436/501; 436/518; 514/9; 514/11; 530/333; 530/334
(58) Field of Search ........................... 514/9.11; 424/177; 530/333, 334, 317; 435/7.1, 72; 436/501, 518

(56) References Cited

U.S. PATENT DOCUMENTS 5,849,691 * 12/1998 Majer et al. .............................. 514/9

OTHER PUBLICATIONS

Hermkens et al. Tetrahedron, vol. 52, No. 13, pp. 4527–4534, Mar. 1996.*

Richter, L. S.; Tom, J. Y. K.; Burnier, J. P. Tet. lett. 1994, 35, pp. 5547–5550 Peptide–Cyclizations on Solid Support: A Fast and Efficient Route to Small Cyclopeptides.

Dutta, A. S. ; Gormley, J. J. ; McLachlan, P. F.; Major, J. S., J. Med. Chem 1990, 33, pp. 2560–2568 Ihnibitors of Human Renin. Cyclic Peptide Analogues Containing a D–PHE–LYS–D–TRP Sequence.

* cited by examiner

Primary Examiner—Jyothsna Venkat
Assistant Examiner—Maurie E. Garcia
(74) Attorney, Agent, or Firm—Kenneth J. Dow

(57) ABSTRACT

The preparation of 14-membered macrocycles from a resin-bound orthogonally protected lysine residue is described. Reductive alkylation of the a-nitrogen followed by acylation with an Fmoc-aminoacid provides a protected dipeptide precursor. Removal of the Fmoc-group, acylation with a succinic anhydride, methyltrityl-group removal and macro-cyclization provides the desired macrocycles, after TFA cleavage, in excellent yield and purity.

5 Claims, No Drawings

SOLID-PHASE SYNTHESIS OF NOVEL 14-MEMBERED MACROYCLES FOR HIGH THROUGHPUT SCREENING

CROSS REFERENCE TO RELATED APPLICATION

This Application claims priority of provisional application Ser. No. 60/081,501, filed Apr. 13, 1998.

BACKGROUND OF THE INVENTION

The application of solid-phase combinatorial chemistry and parallel synthesis techniques for the preparation of non-peptide drug-like molecules has greatly expanded the diversity of agents available for biological screening in the pharmaceutical industry. There has been considerable effort to increase the size and diversity of corporate sample collections to feed HTS (high throughput screening) programs. HTS can potentially deliver a plethora of lead structures, active in novel therapeutic targets, for the medicinal chemist to explore. While there have been many reports in the literature describing methods to prepare acyclic and cyclic (5-, 6- and 7-membered cycles and fused-cycles) compound libraries for HTS; as well as for lead optimization programs, there has been few reports describing the solid-phase synthesis of macrocylic compound libraries.[1] To achieve a truly diverse sample collection for screening, it is desirable that the sample collection contain molecules of varying degrees of conformational flexibility as listed in table I.

TABLE I

| Molecules | Conformational Flexibility | Examples |
|---|---|---|
| Acyclic | High | oligonucleotides[1a], peptides[1b], peptoids[1c], b-peptoids[1d], oligocarbamates[1e] |
| Macrocyclic | Medium | cyclic peptides[1f], macrocycles[1g] |
| Cyclic | Low | benzodiazepines[1h], hydantoins[1i], diketopiperazines[1j], 2-alkylthiobenzimidazoles[1k] |

Acyclic molecules, because they can adopt multiple low energy conformations, would be expected to be fairly promiscuous and provide a higher hit rate relative to the more restricted molecules. Acyclics; however, provide little information about the required spatial arrangement of pharmacophoric groups. On the other hand, cyclic conformationally restricted molecules would be expected to provide valuable structural information concerning the binding requirements. Macrocylic compounds, neither completely rigid nor flexible, would be unique in their coverage of 3-d space and would be a valuable addition to our sample collection. The fact that cyclic peptides have long been of interest due to their attractive biological profile provides further incentive for synthetic investigation. It has been well documented that cyclic peptides often display increased selectivity, better bioavailability, and less susceptibility to proteolytic degradation than corresponding polypeptides. The preparation of cyclic peptides on a solid support has been established as an efficient method of synthesis that avoids undesired cross coupling reactions common to macrocyclization by providing a "pseudo-diluted" environment.[2]

SUMMARY OF THE INVENTION

The invention relates to an efficient solid-phase synthesis of novel 14-membered ring dipeptide derived macrocycles from readily available building blocks.[3] Thus, the invention relates to a process for preparing a macrocyclic compound selected from those of the formula:

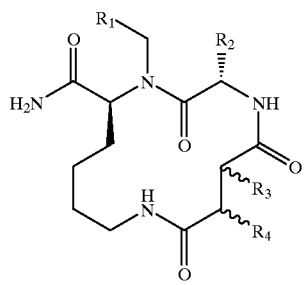

wherein:

R$_1$ is selected from naphthyl, diphenyl, and phenoxyphenyl;

R$_2$ is selected from C$_1$–C$_6$ alkyl, benzyl, C$_1$–C$_6$ alkylamino, CH$_2$SCH$_2$Ph, and CH$_2$(4-MeO)Ph;

R$_3$ is selected from hydrogen and C$_1$–C$_6$ alkyl; and

R$_4$ is selected from hydrogen, phenyl, C$_1$–C$_6$ alkyl;

or R$_3$ and R$_4$ taken together form a 5–6 membered carbocyclic ring; which comprises:

preparing a resin-bound protected dipeptide precursor of the formula:

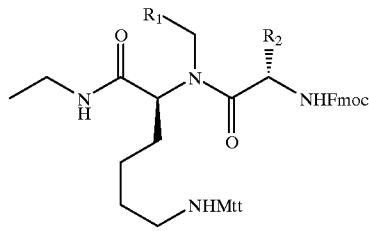

from a resin-bound orthogonally protected lysine residue by reductive alkylation of the α-nitrogen followed by acylation with an Fmoc-aminoacid to provide the protected dipeptide precursor; and removing the Fmoc-group, acylating with a succinic anhydride, removing the methyltrityl-group followed by macrocyclization to provide the desired macrocycle of formula I.

This approach uses the side-chain functionality of lysine in the final ring closure.[4] In addition, this route proved well suited for sort and mix combinatorial chemistry.[5] With the IRORI microkans and our visual tagging method, a diverse three dimensional library of 500 single pure compounds was generated.[6,7]

DETAILED DESCRIPTION

In accordance with the invention, the preparation of 14-membered macrocycles (6) from a resin-bound orthogonally protected lysine residue is described. Reductive alkylation of the α-nitrogen followed by acylation with an Fmoc-aminoacid provides a protected dipeptide precursor (3). Removal of the Fmoc-group, acylation with a succinic anhydride, methyltrityl-group removal and macrocyclization provides the desired macrocycles, after TFA cleavage, in excellent yield and purity.

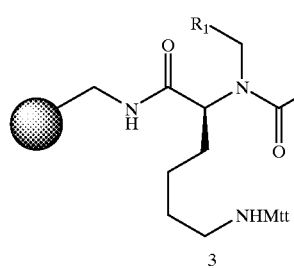

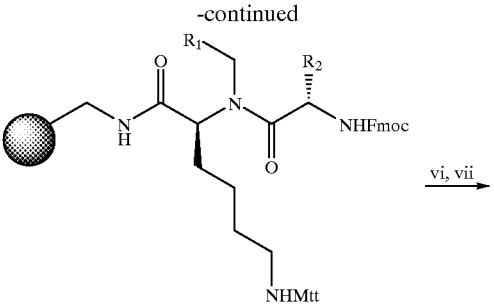

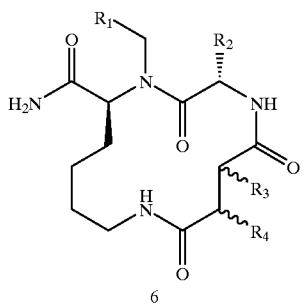

Throughout this specification, certain abbreviations are employed having the meanings as defined therein and as follows, unless specifically indicated otherwise. Fmoc is 9-fluorenylmethyl carbonate, Mtt is methyltrityl, DMF is N,N-dimethyl formamide, MeOH is methanol, THF is tetrahydrofuran, DIEA is diisopropylethylamine, HATU is O-(7-azabenzotriazol-1-yl)-1,1,3,3-tetramethyluroniumhexafluorosulfate.

Scheme I

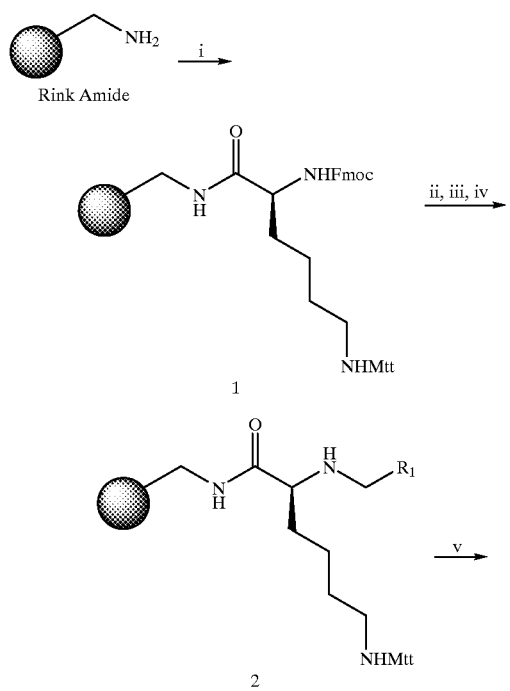

Reagents: (i) Fmoc-Lys(Mtt)-OH, DIC, DCM; (ii) Piperidine-DMF (20%); (iii) $R_1$CHO,TMOF; (iv) Na(OAc)$_3$BH, HOAc, DCM; (v) FmocNH-CH($R_2$)—COOH, DIC, DCM; (vi) Piperidine/DMF (20%); (vii) substituted succinic anhydride, DIEA, DMF; (viii) TFA:TES:DCM (1.3:5:93.7) then DIEA, DCM; (ix) DPPA, DIEA, DMF; (x) TFA:TES:DCM (10:2:88).

The preparation of target macrocycles 6 are illustrated in scheme 1. Initially, protected orthogonally lysine was loaded onto the rink amide solid support using diisopropylcarbodiimide (DIC), followed by selective removal of the Fmoc protecting group.[8] Reductive alkylation of compound 1 proceeded by forming the imine first with an aldehyde in trimethylorthoformate (TMOF), followed by treatment with Na(OAc)$_3$BH and a catalytic amount of HOAc in dichloromethane. Complete reductive alkylation was confirmed by the (Kaiser) ninhydrin test and then the resultant secondary amine coupled with an Fmoc-amino acid using DIC.[9] Subsequent removal of the Fmoc protecting group and reaction with a substituted succinic anhydride in the presence of diisopropyldiethylamine (DIEA) in DMF afforded compound 4.[10] In the next step, the methyltrityl protecting group on the lysine side chain was removed with dilute trifluoroacetic acid (TFA) and triethylsilane (TES).[11] The macrocyclization was carried out with diphenylphosphorylazide (DPPA) and DIEA at room temperature in DMF. In general this reaction, also monitored by (Kaiser) ninhydrin test, was complete within 12 hours. The macrocyclization was also studied with several other reagents like O-(7-azabenzotriazol-1-yl)-N,N,N'N'-tetramethyluroniumhexafluorophosphate (HATU), benzotriazole-1-yl-oxy-tris-pyrrolidino-phosphonium hexafluorophosphate (PyBOP) and pentafluorophenyldiphenylphosphinate (FDPP), but none of them was as effective as DPPA. During the entire sequence, aliquots of resin were cleaved in order to confirm products and purity, and monitor the progress of the reactions. The products were analyzed by ESI mass spectra and HPLC. Treatment of the resin-bound macrocycle with TFA cleaved the desired products 6 from the solid support in excellent yield and purity. A representative sample (table II) was then fully characterized by $^1$H NMR, HPLC and MS.[12]

In summary, an efficient solid-phase synthesis of 14-membered macrocycles with three diversity points has been developed by a "side to tail" cyclization mode using DPPA. The three points of diversity are derived from readily available starting materials—aldehydes, Fmoc aminoacids and substituted succininc anhydrides. The crude products after cleavage from the resin are obtained in yields of 71–99% and purities of 62–98%.

REFERENCES AND NOTES 1. a) Wyatt, J. R.; Vickers, T. A.; Roberson, J. L.; Buckheit, J. R. W.; Klimkait, T.; DeBaets, E.; Davis, P. W.; Rayner, B.; Imbach, J. L.; Ecker, D. J. Proc. Natl. Acad. Sci. 1994, 91, 1356–1360. b) Owens, R. A.; Gesellchen, P. D.; Houchins, B. J.; DiMarchi, R. D. Biochem. Biophys. Res. Commun. 1991, 181, 402–408. c) Zuckermann, R. N.; Kerr, J. M.; Kent, S. B. H.; Moss, W. H. J. Am. Chem. Soc. 1992, 114, 10646–10649. d) Hamper, B. C.; Kolodziej, S. A.; Scates, A. M.; Smith, R. G.; Cortez, E. J. Org. Chem. 1998, 63, 708–718. e) Cho, C. Y.; Moran, E. J.; Cherry, S. R.; Stephans, J. C.; Fodor, S. P. A.; Adams, C. L.; Sundaram, A.; Jacobs, J. W.; Schultz. P. G. Science, 1993, 261, 1303–1305. f) Richter, L. S.; Tom, J. Y. K.; Burnier, J. P. Tet. Lett. 1994, 35, 5547–5540. g) Kenichi, A.; Yoshiaki, K. Tet. Lett. 1997, 38, 5185–5188. h) Bunin, B. A.; Ellman, J. A. J. Am. Chem. Soc. 1992, 114, 10997–10998. i) Matthews, J.; Rivero, R. A.; J. Org. Chem. 1997, 62, 6090–6092. j) Gordon, D. W.; Steele, J. BioMed. Chem. Lett. 1995, 5, 47–50. k) Lee, J.; Gauthier, D.; Rivero, R. A. Tet. Lett. 1998, 39, 201–204.

2. Richter, L. S.; Tom, J. Y. K.; Burnier, J. P. Tet. Lett. 1994, 35, 5547–5550 and references sited herein.

TABLE II

14-Membered Ring Macrocycles

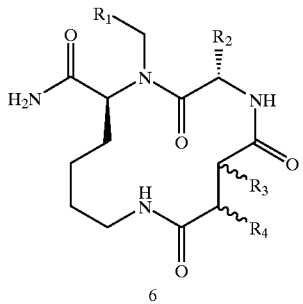

6

| Ex. | $R_1$ | $R_2$ | $R_3$[a] | $R_4$[a] | % Yield[b] | Purity (%)[c] |
|---|---|---|---|---|---|---|
| 6a | 2-Naphthyl | $CH_2Ph$ | H | H | 96 | 98 |
| 6b | 2-Naphthyl | $(CH_2)_4NH_2$ | H | Ph | 98 | 96 |
| 6c | 2-Naphthyl | $(CH_2)_4NH_2$ | H | $CH_3$ | 93 | 86 |
| 6d | 2-Naphthyl | $CH_2CH(CH_3)_2$ | —$CH_2CH_2CH_2CH_2$—[d] | | 99 | 98 |
| 6e | (4-Ph)Ph | $CH_2CH(CH_3)_2$ | H | Ph | 70 | 85 |
| 6f | (4-Ph)Ph | $CH_2Ph$ | H | Ph | 89 | 85 |
| 6g | (4-Ph)Ph | $CH_2SCH_2Ph$ | H | Ph | 77 | 85 |
| 6h | (4-Ph)Ph | $CH_2Ph$ | H | $CH_3$ | 68 | 90 |
| 6i | (4-Ph)Ph | $CH_2SCH_2Ph$ | H | $(CH_3)_2$ | 96 | 70 |
| 6j | (4-PhO)Ph | $CH_2Ph$ | —$CH_2CH_2CH_2CH_2$—[d] | | 99 | 62 |
| 6k | (4-PhO)Ph | $CH_2(4-MeO)Ph$ | H | $CH_3$ | 71 | 90 |

(a) L-Lysine and racemic succinic anhydrides were used, thus the products are a mixture of diastereomers. The regioisomer where the substituent is located at $R_4$ was assigned as the major product. For all of the examples the ratio of regioisomers was between to 1:1 and 2:1.[10]

(b) Yield of crude product after TFA cleavage based on the initial loading to the rink amide resin.

(c) Crude purity after TFA cleavage determined by HPLC (HP ODS Hypersil column), eluent solvent system: 20 to 80% acetonitrile-water containing 0.1% TFA at 220 nm.

(d) The trans cyclohexylsuccinic anhydride was used.

3. There are >500 aromatic aldehydles, >40 finoc amino acids and ca. 35 substituted succinic anhydrides commercially available; theoretically 875,000 compounds can be generated using this methodology.
4. A similar solution phase synthetic approach was used for the preparation of 14-membered macrocyclic renin inhibitors: Dutta, A. S.; Gormley, J. J.; McLachlan, P. F.; Major, J. S. J. Med. Chem. 1990, 33, 2560–2568.
5. The use of radiofrequency tags in the IRORI microkans is described in: Xiao, X-Y.; Parandoosh, Z.; Nova, M. P. J. Org. Chem. 1997, 62, 6029–6033.
6. Our use of visual tags in the microkans is described in: Guiles, J. W.; Lanter, C. L.; Rivero, R. A. Angew. Chem., Int. Ed. Engl. 1998, in press.
7. During the synthesis of the 500 compound library 12.5% of the compounds were evaluated by HPLC and MS and 92% of them were greater than 70% pure and had the expected mass. The eleven examples in table II are representatives from the library that were scaled up to obtain the accurate yields listed in the table.
8. Novabiochem's Rink-amide resin meshed to 100–200 was used in the microkans.
9. Kaiser, E.; Colescott, R. L.; Bossinger, C. D.; Cook, P. I. Anal. Biochem. 1970, 34, 595–598.
10. Based on the HPLC traces obtained, the regioisomeric ratio was found to be between 1:1 and 2:1. The major regioisomer was assigned as the isomer where the substituent is located at $R_4$. Similar regioisomeric ratios were observed during acylations with substituted succinic anhydrides in: (a) Bauer, U.; Ho, W-B.; KoskinenA. M. P. Tet. Lett. 1997, 38, 7233–7236. (b) Robinson, R. P.; Ragan, J. A.; Cronin, B. J.; Donahue, K. M.; Lopresti-Morrow, L. L.; Mitchell, P. G.; Reeves, L. M.; Yocum, S. A. BioMed. Chem. Lett. 1996, 6, 1719–1724.
11. Care was taken not to over-expose the resin-bound intermediate to the mild acid conditions or premature cleavage from the support was observed. A mixture of 1.3% TFA and 5% TES in DCM was added repeatedly to the resin for periods of 1 hour until the Mtt byproduct was no longer detected by HPLC and MS. In general, Mtt removal was complete after 2 hours.
12. The spectral data ($^1$HNMR, ESI MS) of all the products described in table II was consistent with the structure assigned.

Compound 6a: $^1$HNMR (600 MHz, DMSO-$d_6$ at 300° K.) d 8.65 (d, 1H, CH$\underline{NH}$CO), 7.88 (m, 2H, Naph), 7.85 (d, 1H, Naph), 7.82 (s, 1H, Naph), 7.70 (s, 1H, NH$_2$), 7.68 (d, 1H, CH$_2\underline{NH}$CO), 7.55 (m, 2H, Naph), 7.50 (d, 1H, Naph), 7.20 (s, 1H, NH$_2$), 6.88 (t, 1H, Ph), 6.65 (t ,2H, Ph), 6.00 (d, 2H, Ph), 5.42 (d, 1H, N$\underline{CH_2}$Naph), 5.35 (dd, 1H, $\underline{CH}$CONH$_2$), 4.90 (d, 1H, N$\underline{CH_2}$Naph), 4.40 (t, 1H, $\underline{CH}$CH$_2$Ph), 3.57 (m, 1H, CH$_2$), 2.73 (d, 1H, $\underline{CH_2}$Ph), 2.67 (m, 1H, CH$_2$), 2.60 (d, 1H, CH$_2$CO), 2.50 (d, 1H, CH$_2$CO), 2.10 (d, 1H, $\underline{CH_2}$Ph), 2.00 (d, 1H, CH$_2$CO), 1.85 (d, 1H, CH$_2$CO),1.80 (m, 1H, CH$_2$), 1.58 (m, 1H, CH$_2$), 1.43 (m, 1H, CH$_2$), 1.24 (m, 2H, CH$_2$), 0.98 (m, 1H, CH$_2$); MS ESI m/z 515 (M+H), (M +calcd) 514.

We claim:

1. A process for preparing a macrocyclic compound of the formula:

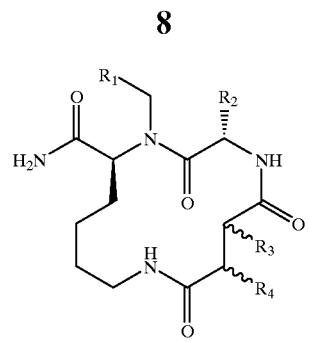

wherein:
$R_1$ is selected from the group consisting of naphthyl, diphenyl, and phenoxyphenyl;
$R_2$ is selected from the group consisting of $C_1$–$C_6$ alkyl, benzyl, $C_1$–$C_6$ alkylamino, CH$_2$SCH$_2$Ph, and CH$_2$(4-MeO)Ph;
$R_3$ is selected from the group consisting of hydrogen and $C_1$–$C_6$ alkyl; and
$R_4$ is selected from the group consisting of hydrogen, phenyl, $C_1$–$C_6$ alkyl;
or $R_3$ and $R_4$ taken together form a 5–6 membered carbocyclic ring;
which comprises:
preparing a resin-bound protected dipeptide precursor of the formula:

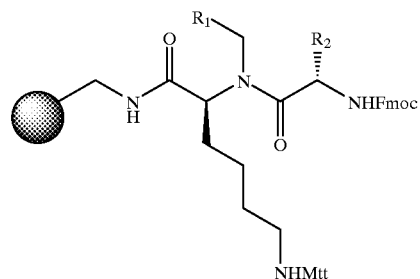

from a resin-bound orthogonally protected lysine residue by reductive alkylation of the α-nitrogen followed by acylation with an Fmoc-aminoacid to provide the protected dipeptide precursor; and removing the Fmoc-group, acylating with an appropriately substituted succinic anhydride, removing the methyltrityl-group followed by macrcocyclization to provide the desired macrocycle of formula I.

2. The process of claim 1 wherein the acylation with the substituted succinic anhydride is conducted in the presence of diisopropyldiethylamine in dimethylformamide.

3. The process of claim 1 wherein the methytrityl protecting group is removed by reaction with dilute triflouroaceticacid and triethylsilane.

4. The process of claim 1 wherein the macrocyclization is carried out with a reagent selected from the group consisting of diphenylphosphorylazide (DPPA), O-(7-azabenzotriazol-1-yl)-N,N,N'N'-tetramethyluroniumhexafluorophosphate (HATU), benzotriazole-1-yl-oxy-tris-pyrrolidino-phosphonium hexa-fluorophosphate (PyBOP) and pentafluorophenyldiphenylphosphinate (FDPP).

5. The process of claim 4 wherein the macrocyclization is carried out with diphenylphosphorylazide (DPPA) and diisopropylethylamine (DIEA) at room temperature in dimethylformamide.

* * * * *